US005490971A

United States Patent [19]
Gifford et al.

[11] Patent Number: 5,490,971
[45] Date of Patent: Feb. 13, 1996

[54] CHEMICAL DETECTOR

[75] Inventors: Michael M. Gifford, Rochester; Kevin J. Mackie, Mansfield, both of Mass.

[73] Assignee: Sippican, Inc., Marion, Mass.

[21] Appl. No.: 328,461

[22] Filed: Oct. 25, 1994

[51] Int. Cl.$^6$ .................................................. G01N 21/01
[52] U.S. Cl. ........................ 422/58; 422/61; 422/82.05; 422/82.08; 422/82.09; 422/86; 422/88; 422/91; 422/101; 422/102; 436/124; 436/125; 436/126; 436/164; 436/165; 436/167; 436/168; 436/172; 436/178
[58] Field of Search .......................... 422/58, 61, 82.05, 422/82.09, 86, 88, 91, 101, 102, 82.08; 436/124, 125, 126, 164, 165, 167, 168, 172, 178; 220/253, 346, 347, 351, 371, 373; 215/261

[56] References Cited

U.S. PATENT DOCUMENTS

| | | | |
|---|---|---|---|
| 3,521,784 | 7/1970 | Gaines et al. | 215/261 |
| 3,865,548 | 2/1975 | Padawer | 436/165 |
| 4,235,839 | 11/1980 | Vesterberg | 422/58 |
| 4,522,923 | 7/1985 | Deutsch et al. | 422/58 |
| 4,666,672 | 5/1987 | Miller et al. | 422/68 |
| 4,771,006 | 9/1988 | Miller et al. | 436/126 |
| 4,790,857 | 12/1988 | Miksch | 422/61 |
| 4,889,992 | 12/1989 | Hoberman | 436/165 |
| 4,929,562 | 9/1990 | Anderson et al. | 436/126 |
| 4,976,923 | 12/1990 | Lipsky et al. | 436/135 |
| 5,119,830 | 6/1992 | Davis | 422/58 |
| 5,310,523 | 5/1994 | Smethers et al. | 422/58 |
| 5,403,551 | 4/1995 | Galloway et al. | 422/102 |

FOREIGN PATENT DOCUMENTS

| | | |
|---|---|---|
| WO93/0438 | 3/1993 | WIPO . |
| 9304368 | 3/1993 | WIPO . |
| 9407127 | 3/1994 | WIPO . |

OTHER PUBLICATIONS

Lugg, "Fujiwara Reaction and Deformation of Carbon Terachloride, Chloroform, Tetrachloroethane, and Trichloroethylene in Air", *Analytical Chemistry*, vol. 38, No. 11, Oct. 1966, pp. 1532–1536.

*Primary Examiner*—James C. Housel
*Assistant Examiner*—Sharidan Carrillo
*Attorney, Agent, or Firm*—Testa, Hurwitz & Thibeault

[57] ABSTRACT

Apparatus for chemical detection includes a cap for coupling with a sample vial containing a sample. The sample includes at least one chemical to be detected. The cap includes a reagent vial which contains a liquid reagent. The reagent vial includes a membrane which substantially retains the liquid reagent and which is substantially permeable to the chemical to be detected. The reagent vial can be opened to allow the chemical to permeate and enter the reagent vial and closed to substantially prevent the chemical from permeating the membrane and entering the reagent vial. In some embodiments, the reagent vial is opened and closed by movement of the reagent vial. In some other embodiments, the reagent vial remains stationary while a device moves to open and close the stationary reagent vial.

62 Claims, 5 Drawing Sheets

CHEMICAL DETECTOR

FIELD OF THE INVENTION

This invention relates to chemical detectors and, more particularly, detectors for the detection of chemicals in a sample contained in a sample vial.

BACKGROUND OF THE INVENTION

The detection and quantification of chemicals is important for health and environmental reasons. For example, it is desirable to detect chemicals such as aromatic and halogenated hydrocarbons, several of which are known carcinogens. Halogenated hydrocarbons include trichloroethylene (TCE), 1,1,1-trichloroethane (TCA), 1,1,2,2-tetrachloroethane, chloroform ($CHCl_3$), carbon tetrachloride ($CCl_4$), and 1,2-dichloroethylene (DCE).

The Fujiwara reaction is a well-known method for detecting and monitoring the presence of chemicals. The reaction can be a two-phase procedure or a one-phase procedure. The Fujiwara reaction is described in, for example, U.S. Pat. Nos. 4,929,562 (issued May 29, 1990), 4,771,006 (issued Sep. 13, 1988), and 4,666,672 (issued May 19, 1987). It also is described in, for example, International Publication No. WO 93/04368 and an article by G. A. Lugg which appeared in *Analytical Chemistry*, pages 1532–36, Vol. 38, No. 11, Oct. 1966.

A detector is needed which can quickly and easily detect chemicals in a sample placed in a sample vial. The detector should be able to detect a variety of different chemicals or analytes.

SUMMARY OF THE INVENTION

The invention generally relates to the optical detection of analytes. A cap is provided which can be coupled with a sample vial containing a sample. The sample includes at least one chemical to be detected. Note that these chemicals to be detected are also referred to herein as analytes. The cap includes a reagent vial which contains a reagent. The reagent vial includes a membrane which substantially retains the liquid reagent and which is substantially permeable to the chemical to be detected. The reagent vial can be opened to allow the chemical to permeate and enter the reagent vial and closed to substantially prevent the chemical from permeating the membrane and entering the reagent vial. In some embodiments, the reagent vial is opened and closed by movement of the reagent vial. In some other embodiments which are presently preferred, the reagent vial remains stationary while a device moves to open and close the stationary reagent vial.

The sample can be a liquid sample from which vapors emanate into a headspace. The one or more chemicals to be detected are included in the vapors, and the chemical(s) can comprise aromatic and/or halogenated hydrocarbons. The reagent can be reactable with the chemical(s) to form a reaction product which has at least one detectable property related to the concentration(s) of the chemical(s). The reaction product can, for example, absorb and emit electromagnetic radiation at an intensity proportional to the concentration(s) of the chemical(s). When open, the chemical included in the vapors is allowed to enter the reagent vial and react with the reagent to form the reaction product. The membrane generally holds both the liquid reagent and the reaction product inside the reagent vial, regardless of whether the reagent vial is open or closed.

In some embodiments in which the sample is a liquid with analytes (e.g., solids such as metals) dissolved or suspended therein, there is no headspace. Instead, the sample directly contacts the membrane, and the analyte(s) of interest permeate the membrane and enter into the reagent vial when the reagent vial is in the open position.

After the sample is placed in the sample vial, the cap is placed on the sample vial. If both the cap and the sample vial are threaded, the cap is screwed onto the sample vial. The combination of the cap and the sample vial is now insertable into an analyzer. Either before, during, or after insertion of the combination into the analyzer, the reagent vial is placed in the open position such that the vapors from the sample can diffuse into contact with the membrane (or, in other embodiments, such that the sample can directly contact the membrane). The chemical to be detected can then permeate through the membrane, and encounter and react with the reagent. The analyzer can then illuminate the reaction product in the reagent vial and determine the concentration of the chemical by detecting, for example, the resulting absorbance or fluorescence of the reaction product. The detection can be done at a single point in time or over a period of time. When the measurement is complete, the combination of the cap and the sample vial can be removed from the analyzer, and the cap can be decoupled from the sample vial.

Caps containing different reagents can be provided to allow a variety of chemicals to be detected. The cap is relatively inexpensive. Once the cap is decoupled from the sample vial, it can be discarded, and a new cap can be selected and used in the next detection. Alternatively, the reagent vial can be removable from the cap such that it is discarded and the cap is reused. In this alternative embodiment in which the reagent vial is the consumable item (as opposed to the entire cap assembly being the consumable item), a new reagent vial is placed in the reusable cap to prepare for the next detection.

The analyzer can include a light source for illuminating the reaction product to cause the reaction product to produce one or more optical signals. The optical signal(s) can be representative of the absorbance or the fluorescence of the reaction product. The analyzer also can include one or more optical detection elements for receiving the optical signal(s) and generating one or more other signals related thereto. Electronics in the analyzer can receive and manipulate the signal(s) generated by the detection element(s) to determine a numerical value for the concentration(s). The analyzer also can include a motor for magnetically coupling with and driving a mixing device in the reagent vial which stirs the contents of the reagent vial. The reagent can be a Fujiwara reagent, and the reaction product thus can be the result of a Fujiwara reaction. The Fujiwara reagent is a mixture of pyridine (or a pyridine derivative), water, and a base. Other reagents useful in determining analyte species also can be employed. For example, the BTEX reagent, $H_2SO_4$—$CH_2O$, can be used.

The invention provides a simple and easy-to-use chemical concentration measurement system. No chemistry is required to make a measurement of chemical concentration. Prior to use, the reagent vials, whether removable from a reusable cap or fixed in a non-reusable cap, are individually loaded with reagent sufficient for a single measurement. Various reagents can be loaded into the reagent vials. The expendable component of the system, whether the entire cap or a removable reagent vial, is inexpensive thereby making the system a cost effective chemical concentration measurement device. The cap, whether reusable or not, and the analyzer are both field portable, and the system greatly simplifies field measurements.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
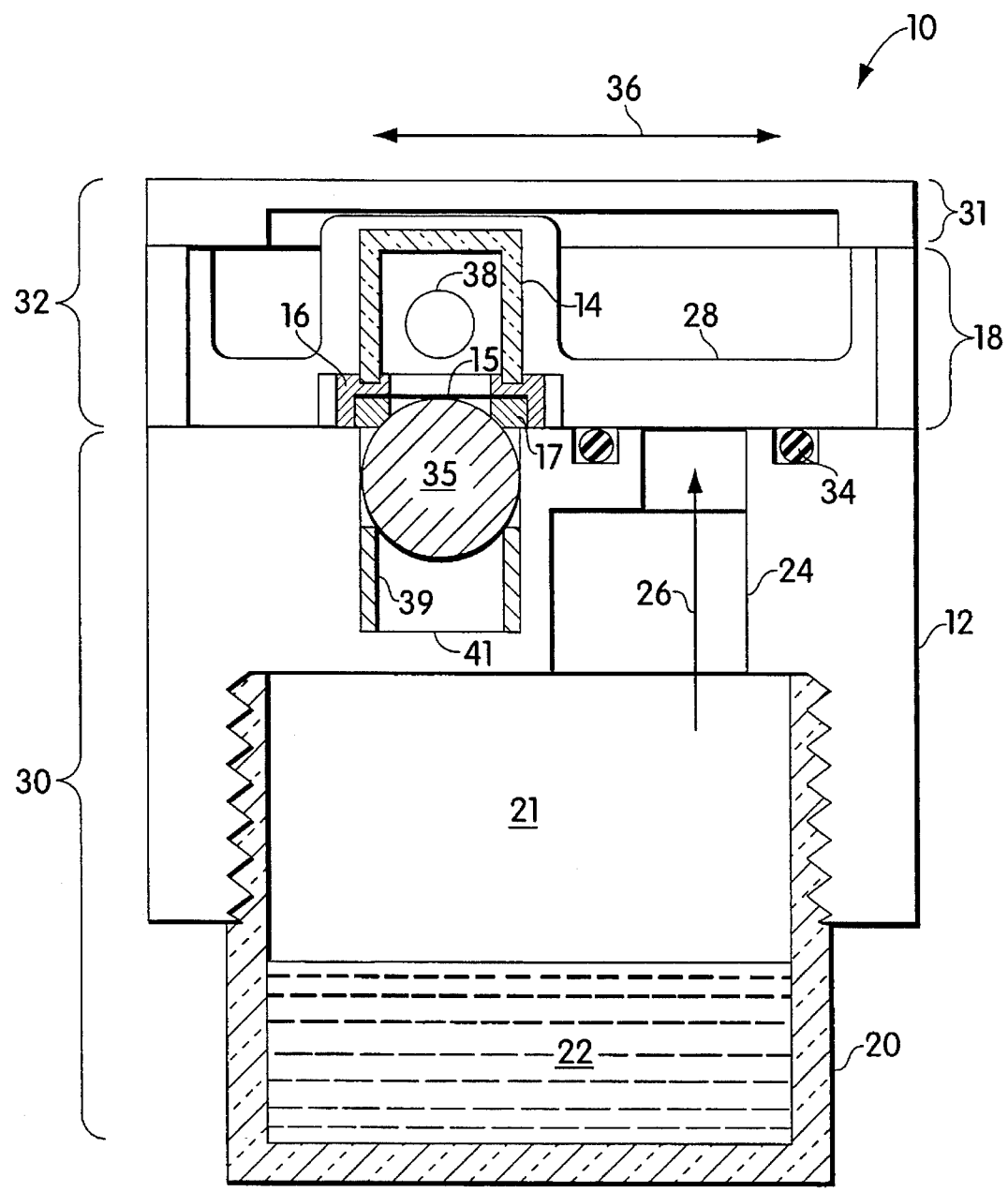
FIG. 1A is a diagram in partial cross-section of an embodiment of a chemical detection device according to the invention with a reagent vial in a closed position.
Figure 1B:
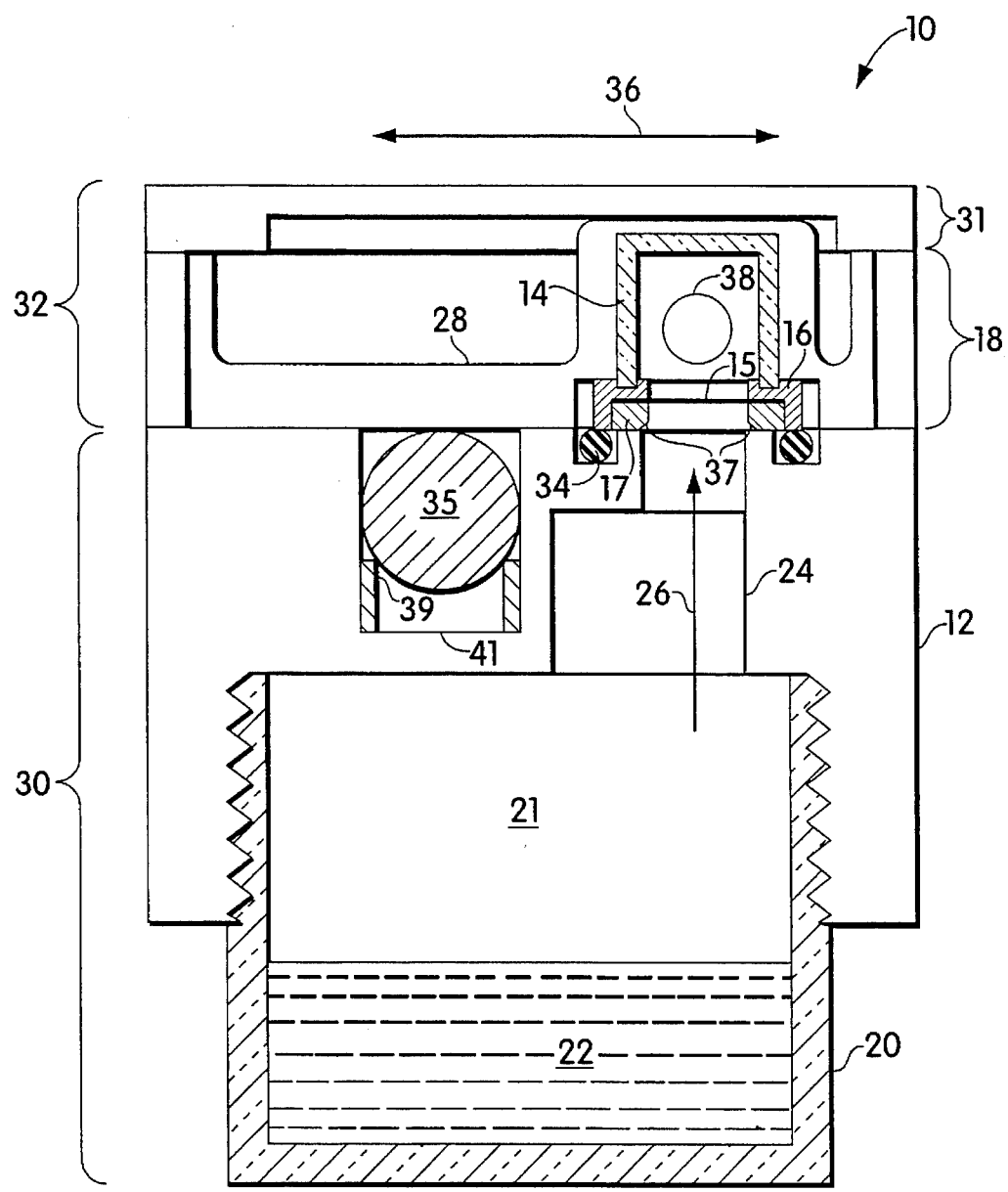
FIG. 1B is a diagram in partial cross-section of the chemical detection device of FIG. 1A with the reagent vial in an open position.
Figure 2:
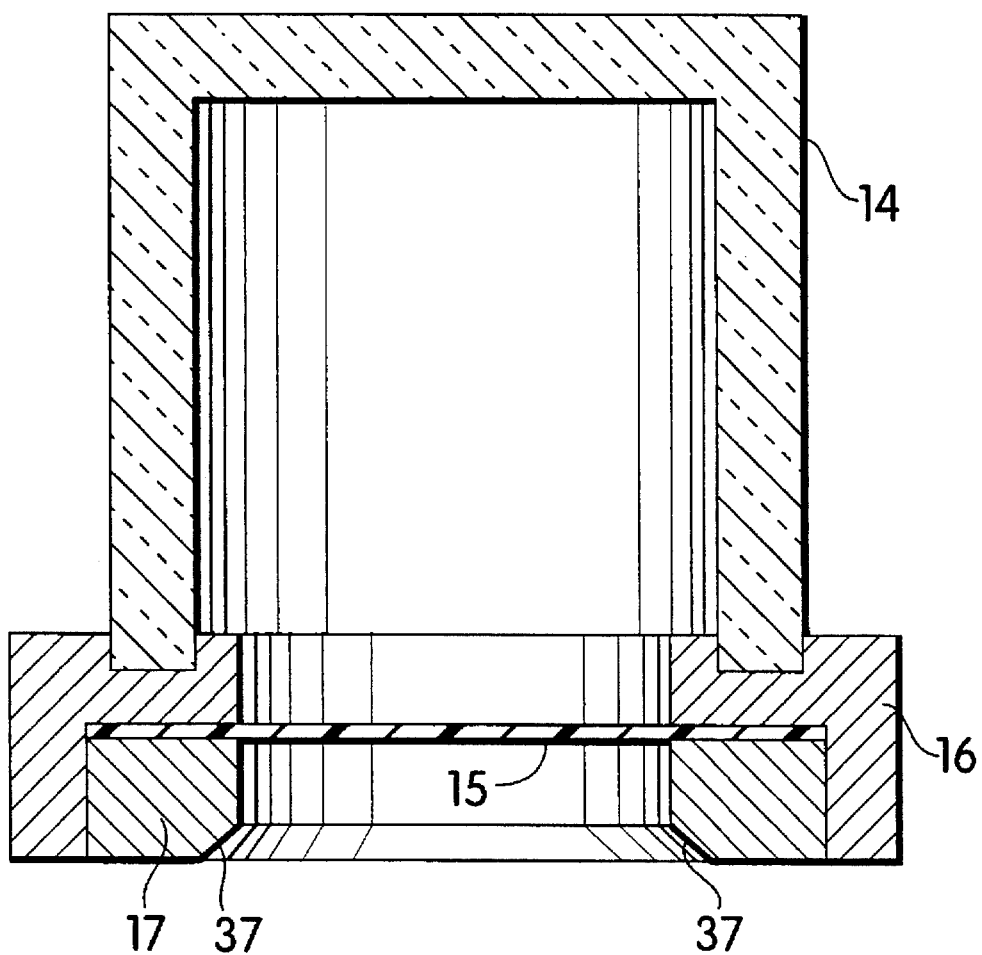
FIG. 2 is an enlarged view of the reagent vial of FIGS. 1A and 1B.

Referring to FIGS. 1A and 1B, an embodiment of a chemical detection device 10 according to the invention includes a cap 12 having a movable reagent vial 14 as part thereof. In this embodiment, the reagent vial 14 is moved by sliding a slide 18 between a first, closed position (FIG. 1A) and a second, open position (FIG. 1B). In other embodiments, the reagent vial 14 can be moved between the open and closed positions by rotation of the slide 18, e.g., by a one-quarter turn rotation of the slide 18. The reagent vial 14 contains a reagent which is retained within the reagent vial 14 by the enclosing sides and top of the reagent vial 14 and by a membrane 15 which forms the bottom of the reagent vial 14. Note that the reagent is contained within the the reagent vial 14 regardless of the reagent vial's position or the means by which the reagent vial is moved between the open and closed positions. The reagent remains within the reagent vial 14 because the membrane 15 retains the reagent therewithin. The membrane 15 is attached to the walls of the reagent vial 14 by an inner washer 16 and an outer washer 17, where the membrane 15 is sandwiched between the inner and outer washers 16, 17. The membrane 15 is described in greater detail hereinafter. An enlarged view of the reagent vial 14 is shown in FIG. 2. The structure of the reagent vial 14 is clear from the enlarged view provided in FIG. 2.

Still referring to FIGS. 1A and 1B, the cap 12 is couplable with a sample vial 20. In this embodiment, the coupling is achieved by screwing a threaded portion of the sample vial 20 into a threaded portion of the cap 12. It is possible to use a variety of other coupling techniques. Before the sample vial 20 is coupled to the cap 12, a sample 22 to be tested is placed in the sample vial 20. The sample 22 typically is a liquid sample from a source suspected of being contaminated with one or more halogenated hydrocarbons, organo-halogens, and organic chlorides such as trichloroethylene (TCE), 1,1,1-trichloroethane (TCA), 1,1,2,2-tetrachloroethane, chloroform ($CHCl_3$), carbon tetrachloride ($CCl_4$), and 1,2-dichloroethylene (DCE). With the sample 22 in the sample vial 20 and the sample vial 20 coupled to the cap 12, vapors diffuse from the sample 22, enter a headspace, and travel up into a passage 24 defined in the cap 12. The path which the vapors take through the passage 24 is indicated generally by an arrow 26. The headspace generally is the space above the top surface of the sample 22, and it is indicated by the reference numeral 21 in FIGS. 1A and 1B. The vapors include one or more chemicals to be detected, and the chemical(s) can include a variety of substances and pollutants such as those mentioned previously.

The sample can be a liquid sample having analytes (e.g., solids such as metals) dissolved or suspended therein. In these cases, there is no headspace, and the sample directly contacts the membrane 15. The analyte(s) of interest in the sample permeate the membrane and enter into the reagent vial 14 when the reagent vial is in the open position.

The membrane 15 is permeable or substantially permeable to chemicals to be detected. The membrane 15 also is somewhat impermeable to the liquid reagent in the reagent vial 14. That is, while the membrane 15 is effective in retaining the liquid reagent within the reagent vial 14, it is possible that some reagent can penetrate or leak through the membrane 15. Note that the reagent vial 14 typically is in the closed position (FIG. 1A) more often than it is in the open position (FIG. 1B), and any reagent which does leak through the membrane 15 is prevented from entering the sample vial 20 when the reagent vial 14 is in the closed position. The membrane 15 thus is semipermeable because it is largely impermeable to the liquid reagent but permeable to the chemicals of interest. Possible membrane materials include thin paraffin films, mylar, teflon, silicones, inorganic oxides, porous stainless steel, and polycarbonate films. The membrane material is selected based on the particular reagent and the particular chemicals to be detected.

When the reagent vial 14 is in the open position (FIG. 1B), the chemical or analyte of interest can permeate the membrane 15 and enter the interior of the reagent vial 14 wherein the reagent is located. The chemical or analyte reacts with the reagent to form a reaction product. The reaction product has at least one detectable property which is related to the concentration (i.e., amount per unit volume) of the chemicals of interest. For example, the reaction product can fluoresce or absorb light when illuminated. The magnitude of the fluorescence or absorbance is related to the concentration. As described in more detail hereinafter, light can be directed into the reagent vial 14 through a window 38 in the cap 12 in order to illuminate the reaction product. While not shown, the cap 12 preferably has two such windows, one on either side such that light can be directed into one side of the cap 12 and reagent vial 14 and resulting optical effects (e.g., absorbance) can be detected on the other side of the reagent vial 14. Other optical configurations can be used to detect other optical effects (e.g., fluorescence and/or backscatter can be detected from the same window through which light is directed).

When the reagent vial 14 is in the closed position as shown in FIG. 1A, it is disposed from the passage 24, and the chemicals of interest (indicated by the arrow 26) cannot permeate the membrane 15. In fact, sliding structure 28 blocks the vapors emanating from the sample 22 in the sample vial 20. That is, the sliding structure 28 keeps the vapors in a bottom portion 30 of the chemical detection device 10 and out of a top portion 32 thereof. An O-ring 34 provides a seal which helps to maintain the vapors in the bottom portion 30 of the device 10 when the reagent vial 14 is in the closed position (FIG. 1A). Note that the top portion 32 includes the slide 18 and a cover 31, and the slide 18 includes the sliding structure 28.

The sliding structure 28 is located in the top portion 32 of the cap 12, and it is movable (e.g., slidable or rotatable, as described previously) to the left and right as indicated by an arrow 36 above the device 10. Movement of the sliding structure 28 causes movement of the reagent vial 14. Movement of the sliding structure 28 is what causes the reagent vial 14 to move between the open and closed positions. In some embodiments, the sliding structure 28 is biased (e.g., with a spring) such that the reagent vial 14 returns to the closed position (FIG. 1A) unless it is held in the open position (FIG. 1B). Also, in some embodiments, the sliding structure 28 can lock into position when it reaches the closed and/or open position and be freely movable when between those two extremes.

In the disclosed embodiment, when the sliding structure 28 and the reagent vial 14 are in the closed position (FIG. 1A), a ball 35 is forced into contact with the outer washer 17, and typically at least a portion of the membrane 15, to seal the reagent vial 14 and prevent anything from escaping from the reagent vial 14 or contacting the membrane 15. The ball 35 contacts a beveled edge 37 of the outer washer 17, which edge 37 is identified with a reference numeral in FIGS. 1B and 2 but not in FIGS. 1A or 3. While it is preferred that the ball 35 be made of steel or teflon, it is possible to make the ball from any of a variety of materials. The ball 35 is biased up into sealing contact with the edge 37 of the outer washer 17 by a spring 39. Other biasing means besides the spring 39 can be used. Both the spring 39 and the ball 35 are disposed in a cavity 41 formed in the cap 12.

When the reagent vial 14 is in the open position as shown in FIG. 1B, it is aligned or substantially aligned with the passage 24, and the chemicals of interest can permeate the membrane 15 and enter the reagent vial 14 to react with the reagent and form the reaction product. In the open position, the sliding structure 28 forces the ball 35 down into the cavity 41 against the force of the spring 39. The ball 35 remains in the cavity 41 until the reagent vial 14 moves, or is moved, back to the closed position and then the spring 39 will force the ball 35 up and into sealing contact with the edge 37 of the outer washer 17. In the open position, the O-ring seals against the inner and/or outer washers 16, 17 and prevents the vapors (arrow 26) from escaping.

In the disclosed embodiment, the reagent vial 14 is made of glass. It is possible to make the reagent vial 14 of a non-light-transmitting material (e.g., metal or plastic), but then it would be necessary for the reagent vial 14 to have windows on either side (like the windows 38 of the cap 12) thereby increasing the cost and complexity of the reagent vial 14. The inner and outer washers 16, 17 can be made of a variety of materials but metal, especially brass, is preferred. The rest of the cap 12 preferably is made of a thermoplastic with metalized surfaces that prevent, or at least inhibit, chemical absorption into the plastic. The cap 12 can be made from a variety of other materials. The sample vial 20 typically will be glass or clear plastic although many other materials are possible. The sample vial 20 preferably has a capacity of 40 milliliters, and in a preferred embodiment, it is a 40 milliliter VOA (Volatile Organics Analysis) sample vial.

Figure 3:
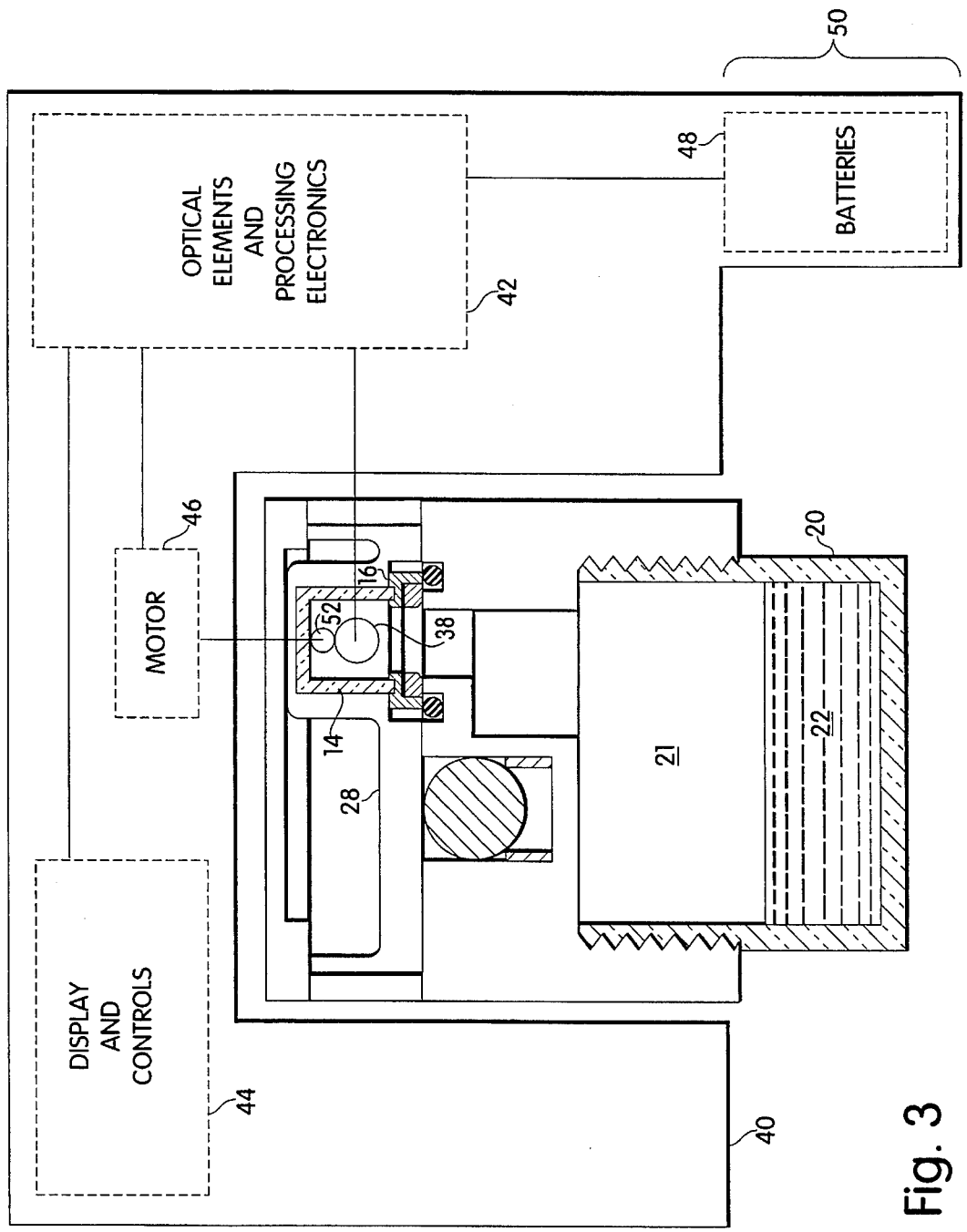
FIG. 3 is a functional block diagram of a chemical detection system with the chemical detection device of FIGS. 1A and 1B.

Referring to FIG. 3, in accordance with the invention, the cap 12 (with the sample vial 20 coupled thereto) can be inserted into a chemical detection system 40. In some embodiments, the act of inserting the cap 12 into the system 40 causes the sliding structure 28 and thus the reagent vial 14 to move to the open position. In some other embodiments, after the cap 12 is received into the system 40, an operator must manually manipulate the sliding structure 28 in order to move the reagent vial 14 from the closed position to the open position shown in FIG. 3. Once the cap 12 is received into the system 40 and the reagent vial 14 is in the open position, the vapors from the sample in the sample vial 20 can impinge upon the membrane 15, and thus the chemicals therein can permeate the membrane 15 and enter the reagent vial 14 to form the reaction product by reacting with the reagent therein.

The system 40 is a chemical analyzer which can illuminate the reaction product when the reagent vial 14 is in the open position, detect the resulting optical effects, and determine therefrom the concentration level of the chemical of interest. The analyzer 40 includes optical elements and processing electronics 42, a display and controls 44, a motor 46, and a battery or batteries 46 for powering the various components. In the disclosed embodiment, the batteries 48 or other power source are disposed in a handle portion 50 of the analyzer 40.

It is important to note that the drawings generally are not to scale and generally are not proportional either. The drawings are meant to convey and emphasize the principles of the invention. The analyzer 40 is depicted in FIG. 3 in a functional block diagram format. Thus, the general physical dimensions and shape of the analyzer 40 will be described herein. The analyzer 40, with or without the cap 12/sample vial 20 attached, is of a hand-holdable, portable size. For example, in the disclosed embodiment, the analyzer 40 is equal to or less than about one cubic foot, preferably 9 inches by 4 inches by 4 inches. The handle portion 50 is designed to be gripped by a user to allow the user to hold the analyzer 40 while operating it. The shape and weight of the analyzer 40 are such that it can be carried easily with one hand. The weight typically is between 2–4 lbs. The housing of the analyzer 40 can be made from a rugged, chemical resistant material such as high density polyethylene (HDPE). The cap 12 is about one inch by one inch by one inch, and the reagent vial 14 is about 0.25 inches by 0.25 inches by 0.25 inches.

Still referring to FIG. 3, the motor 46 in the analyzer 40 is used to drive (e.g., rotate) a mixing device 52 disposed in the reagent vial 14. Movement of the mixing device 52 stirs the contents of the reagent vial 14 to evenly distribute the contents in order to obtain an accurate measurement of the concentration from the reaction product. The motor 46 becomes magnetically coupled to the mixing device 52 when the cap 12 is inserted into the analyzer 40. A line extending from the motor 46 to the mixing device 52 represents the coupling which allows the motor 46 to drive the mixing device 52. In the disclosed embodiment, the mixing device 52 is a ball bearing having a diameter of about $1/32$ inches and being made of, for example, steel. In the disclosed embodiment, the motor 46 is a small DC motor, and the coupling to the ball bearing is magnetic.

The optical elements 42 in the analyzer 40 include a light source for generating light which is directed into the reaction product in the reagent vial 14 through one of the windows 38. The light illuminates the reaction product and causes the reaction product to produce an optical signal, for example, absorbance or fluorescence of the reaction product. In the disclosed embodiment, the light source is a high-intensity, low-voltage tungsten light source. Other types of light sources can be used. The optical elements 42 also include one or more optical detection elements for receiving the optical signal and generating another signal related thereto. In the disclosed embodiment, the optical detection element is disposed opposite the light source on the other side of the cap 12 near the other window 38. The optical detection elements preferably are photodiodes, and two such detection elements are provided in the disclosed embodiment. One of the detection elements is a reference photodiode, and the other one is a measurement photodiode. A beamsplitter directs the optical signal to each of the two photodiodes. A filter preferably is placed between the beamsplitter and each of the two photodiodes. In some embodiments, the filter associated with the measurement photodiode passes substantially only wavelengths of the optical signal in the absorption band of the reaction product, and the filter associated with the reference photodiode passes non-absorbing wavelengths at a defined bandwidth. The reference photodiode provides a reference light level by monitoring the intensity of the light emitted by the light source at a non-absorbed wavelength. The two photodiodes generate signals (e.g., electrical signals) based on the detected optical signal.

The processing electronics 42 in the analyzer 40 receive the signals generated by the two photodiodes over time and manipulate them to determine a numerical value for the concentration. The electronics 42 then cause the display 44 to show the concentration value (e.g., in parts per million or parts per billion) so it can be read by a user. The processing electronics include at least a microprocessor and memory. The display can be a liquid crystal display (LCD). Other types of displays are possible. The user can initiate the measurement and generally control the analyzer 40 by using the controls 44. The controls can include a tactile keypad having, for example, on, off, and calibration. The batteries 48 power the various components of the analyzer 40. The batteries 48 can comprise a rechargeable battery pack that includes, for example, four AA NICAD rechargeable batteries allowing more than forty hours of continuous operation on a single battery charge. A 9 volt DC battery charger (not shown) can be provided with the analyzer 40. AC power or alkaline batteries also can be used as the power source.

In some embodiments, the processing electronics 42 are provided on a circuit card assembly adapted for insertion into a personal computer. In these embodiments, the personal computer would utilize the card to receive data from the analyzer 40 and process the data. A monitor connected to the personal computer can be used to display information such as the concentration value.

As mentioned previously, the reagent in the reagent vial 14 can be a Fujiwara reagent, and the reaction product can be the result of the Fujiwara reaction. The Fujiwara reaction is well-known, and it can be a one-phase procedure or a two-phase procedure. In the disclosed embodiment, a one-phase procedure is employed. When the Fujiwara reagent is exposed to the chemical of interest, the resulting reaction product is a Fujiwara reaction product. Illumination of this reaction product results in absorption and/or fluorescence peaks of the reaction product which can be detected as a function of time. From these data, the processing electronics 42 can determine the concentration of the chemical of interest. For example, the processing electronics can store, in the memory, a lookup table containing absorbance and/or fluorescence values of a variety of known substances, and the detected data from an unknown substance can then be compared with the stored values to determine the type of substance and its concentration in the sample. The lookup table is created ahead of time and acts as a baseline of absorption and/or fluorescence time-phased data for a variety of known substances expected to be encountered in the various samples presented for analysis.

When the measurement is complete, the combination of the cap 12 and the sample vial 20 can be removed from the analyzer 40. The cap 12 can then be decoupled from the sample vial 20 and discarded. The cap is relatively inexpensive to manufacture. Caps having reagent vials which contain different reagents can be supplied to allow a variety of substances to be detected and measured. The cap thus is an expendable or consumable item, and a user selects a new cap for each detection that the user performs.

In some embodiments, the reagent vial 14 can be removable from the cap 12. In these embodiments, it is the reagent vial that is discarded, and the cap is reused. A reagent vial is relatively inexpensive to manufacture. After a detection is complete and the cap is removed from the analyzer, the reagent vial in the cap is removed and discarded, and a new reagent vial is selected and placed into the reusable cap to prepare for the next detection. Thus, in these alternative embodiments, the the reagent vial is the expendable or consumable item as opposed to the entire cap assembly being the consumable item.

The invention provides a simple and easy-to-use chemical concentration measurement system. No chemistry is required to make a measurement of chemical concentration. Prior to use, the reagent vials, whether removable from a reusable cap or fixed in a non-reusable cap, are individually loaded with reagent sufficient for a single measurement-Various reagents can be loaded into the reagent vials. The expendable component of the system, whether the caps or the removable reagent vials, is inexpensive thereby making the system a cost effective chemical concentration measurement device. The cap (whether reusable or not) and the analyzer are both field portable, and the system greatly simplifies field measurements.

It is noted that the reagent vial 14 can be used to concentrate analytes therewithin, and the reagent vial can then be probed to determine the concentration of the analytes whether or not a reaction product is created in the reagent vial. Methods not requiring formation of a reaction product include spectroscopic techniques that probe the optical properties of the analyte molecule including Raman, infra-red (IR), and near-IR (NIR) techniques.

Figure 4A:
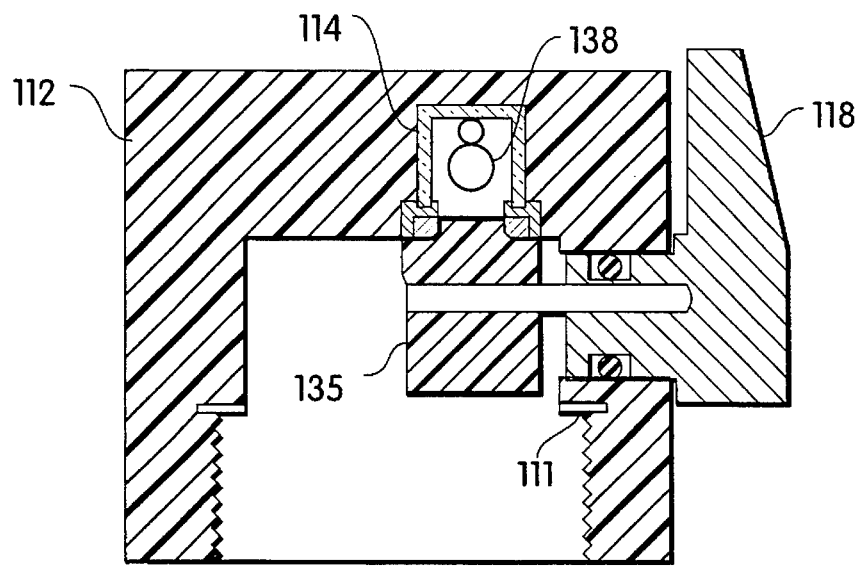
FIGS. 4A and 4B are diagrams in partial cross-section of another embodiment of a chemical detection device according to the invention with a reagent vial closed (FIG. 4A) and opened (FIG. 4B).
Figure 4B:
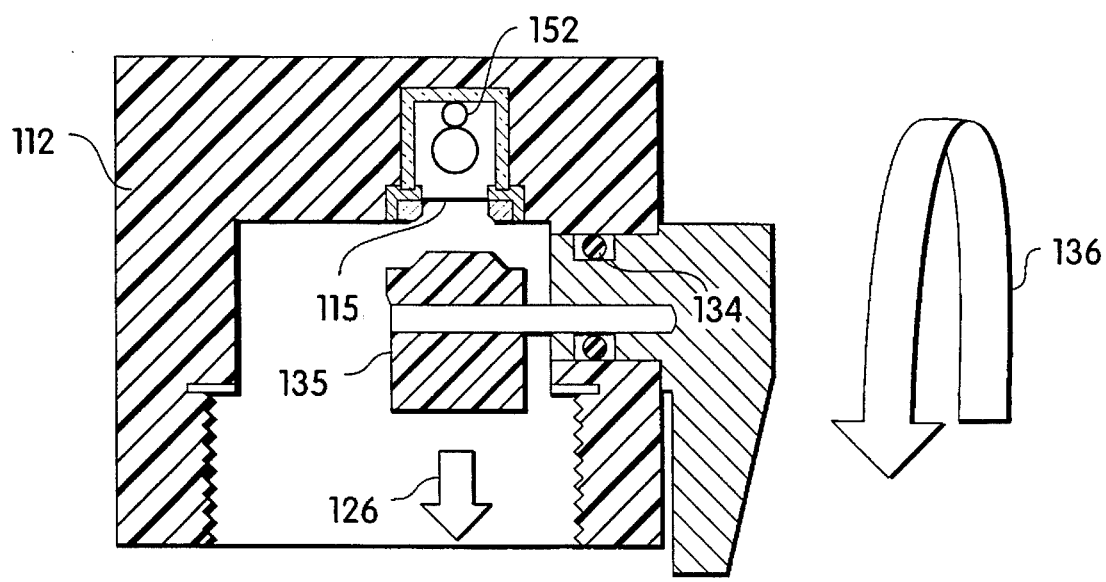

Referring to FIGS. 4A and 4B, another embodiment of a chemical detection device according to the invention includes a cap 112 having a fixed-position reagent vial 114 as part thereof. In this embodiment, which is the presently preferred embodiment, the reagent vial 114 is opened and closed by turning a cam assembly 118 to move a plug 135 between a first, closed position (FIG. 4A) and a second, open position (FIG. 4B). In the disclosed-embodiment of FIGS. 4A and 4B, a one-half turn of the cam assembly 118 moves the plug 135 from the closed position (FIG. 4A) to the open position (FIG. 4B), as indicated by arrows 126, 136. Like the reagent vial 14 of FIGS. 1A, 1B, 2, and 3, this reagent vial 114 contains a reagent which is retained therewithin by the enclosing sides and top thereof and by a membrane 115 which forms the bottom thereof. The reagent is contained within the the reagent vial 114 regardless of the position of the plug 135. The reagent remains within the reagent vial 114 because the membrane 115, like the membrane 15 of FIGS. 1A, 1B, 2, and 3, retains the liquid reagent therewithin. The membrane 115 is attached to the walls of the reagent vial 114 by a washer configuration similar to that describe hereinbefore with reference to FIGS. 1A, 1B, and 2.

The cap 112, like the cap 12 of FIGS. 1A, 1B, 2, and 3, is couplable with a sample vial, but the sample vial is not shown in FIGS. 4A and 4B. The cap 112 can include a gasket 111 to provide a tight seal when the sample vial is coupled to the cap 112. Before the sample vial is coupled to the cap 112, a sample (not shown, but similar to the sample 22 of FIGS. 1A and 1B) to be tested is placed in the sample vial. With the sample in the sample vial and the sample vial coupled to the cap 112, vapors diffuse from the sample and travel up into the cap 112. The vapors include one or more chemicals to be detected, and the chemical(s) can include a variety of substances and pollutants such as those mentioned previously. As also mentioned previously, the sample can be a liquid sample having analytes (e.g., solids such as metals) dissolved or suspended therein, in which case the sample directly contacts the membrane 115. The analyte(s) of interest in the sample permeate the membrane 115 and enter into the reagent vial 114 when the reagent vial 114 is open, i.e., when the plug 135 is away from the reagent vial 114 as in FIG. 4B.

Like the membrane 15, the membrane 115 of FIGS. 4A and 4B is permeable or substantially permeable to chemicals to be detected. The membrane 115 also is somewhat impermeable to the liquid reagent in the reagent vial 114. That is, while the membrane 15 is effective in retaining the liquid reagent within the reagent vial 114, it is possible that some reagent can penetrate or leak through the membrane 115. Note that the reagent vial 114 typically is in the closed position (FIG. 4A) more often than it is in the open position (FIG. 4B), and any reagent which does leak through the membrane 115 is prevented from entering the sample vial (not shown in FIGS. 4A and 4B) by the plug 135 when the reagent vial 114 is in the closed position. The membrane 115 thus is semipermeable because it is largely impermeable to the reagent but permeable to the chemicals of interest. Possible membrane materials are as described previously.

When the plug 135 is in the open position (FIG. 4B), the chemical or analyte of interest can permeate the membrane 115 and enter the interior of the reagent vial 114 wherein the reagent is located. The chemical or analyte reacts with the reagent to form a reaction product. As described previously with reference to FIGS. 1A, 1B, 2, and 3, the reaction product has at least one detectable property which is related to the concentration (i.e., amount per unit volume) of the chemicals of interest, such as fluorescence or absorbance. As described previously, light can be directed into the reagent vial 114 through a window 138 in the cap 112 in order to illuminate the reaction product.

When the plug 135 is in the closed position as shown in FIG. 4A, the chemicals of interest cannot permeate the membrane 115; the plug 135 blocks the vapors emanating from the sample in the sample vial. The top of the plug 135 has indentations or grooves which fit against the bottom of the reagent vial 114 to form a tight seal when the plug 135 is moved into the closed position by action of the cam assembly 118. The plug 135 preferably is made from teflon or stainless steel, although a variety of other materials also can be used for the plug 135.

Movement of the cam assembly 118 causes movement of the plug 135. In some embodiments, the cam assembly 118 is biased (e.g., with a spring) such that the plug 135 returns to the closed position (FIG. 4A) unless it is held in the open position (FIG. 4B). Also, in some embodiments, the cam assembly 118 can be locked into position when it reaches the closed and/or open position and be freely movable when between those two extremes. An o-ring 134 provides a seal to prevent vapors from escaping out of the cap/sample vial assembly when the sample vial is coupled to the cap 112. The materials from which the various components of the cap 112 can be made have been presented previously. The size of the cap 112 is about one inch by one inch by one inch, and the size of the reagent vial 14 is about 0.25 inches by 0.25 inches by 0.25 inches. The cap 112 is about the same size as the cap 12 of FIGS. 1A, 1B, 2, and 3.

Similar to the previous description with reference to FIG. 3, the cap 112 (with the sample vial coupled thereto) can be inserted into the chemical detection system 40. In some embodiments, the act of inserting the cap 112 into the system 40 causes the cam assembly 118 and thus the plug 135 to move to the open position (FIG. 4B). In some other embodiments, after the cap 112 is received into the system 40, an operator must manually manipulate the cam assembly 118 in order to move the plug 135 from the closed position of FIG. 4A to the open position of FIG. 4B. In still some other embodiments, the plug 135 is moved to open up the reagent vial 114 before the cap 112 is inserted into the system 40. In any case, the reaction product is eventually created in the reagent vial 114 and the system 40, having the cap 112 therein, illuminates the reaction product, detects the resulting optical effects, and determines therefrom the concentration level of the chemical of interest in the reagent vial 114. The analyzer 40 is as described previously with reference to FIG. 3.

As described previously, the motor 46 in the analyzer 40 is used to drive (e.g., rotate) a mixing device or stirrer 152 disposed in the reagent vial 114. Movement of the mixing device 152 stirs the contents of the reagent vial 114 to evenly distribute the contents in order to obtain an accurate measurement of the concentration from the reaction product. The motor 46 becomes magnetically coupled to the mixing device 152 when the cap 112 is inserted into the analyzer 40. In the disclosed embodiments, the mixing device 152 and the motor 46 are as described previously.

When the measurement is complete, the combination of the cap 112 and the sample vial can be removed from the analyzer 40. The cap 112 can then be decoupled from the sample vial and discarded. The cap is relatively inexpensive to manufacture. Caps having reagent vials which contain different reagents can be supplied to allow a variety of substances to be detected and measured. The cap thus is an expendable or consumable item, and a user selects a new cap for each detection that the user performs. In some embodiments, the reagent vial 114 can be removable from the cap 112. In these embodiments, it is the reagent vial that is discarded, and the cap is reused. A reagent vial is relatively inexpensive to manufacture. After a detection is complete and the cap is removed from the analyzer, the reagent vial in the cap is removed and discarded, and a new reagent vial is selected and placed into the reusable cap to prepare for the next detection. Thus, in these alternative embodiments, the reagent vial 114 is the expendable or consumable item as opposed to the entire cap assembly 112 being the consumable item.

Variations, modifications, and other implementations of what is described herein will occur to those of ordinary skill in the art without departing from the spirit and the scope of the invention as claimed. Accordingly, the invention is to be defined not by the preceding illustrative description but instead by the following claims.

What is claimed is:

1. Apparatus for chemical detection, comprising:
   a cap for coupling with a sample vial containing a sample which includes at least one chemical to be detected;

a reagent vial included in the cap, the reagent vial containing a liquid reagent and including a membrane which retains the liquid reagent above the membrane, wherein said membrane is permeable to the chemical to be detected; and means, coupled to the cap, for moving the reagent vial between a first position and a second position, the chemical being prevented from permeating the membrane and entering the reagent vial when the reagent vial is in the first position, the chemical being allowed to permeate the membrane and enter the reagent vial when the reagent vial is in the second position.

2. The apparatus of claim 1 wherein the cap is expendable.

3. The apparatus of claim 1 wherein the reagent vial is removable from the cap, and the reagent vial is expendable.

4. The apparatus of claim 1 wherein the apparatus is transportable to allow coupling with the sample vial in the field.

5. The apparatus of claim 4 wherein the size of the cap is about one inch by one inch by one inch.

6. The apparatus of claim 5 wherein the size of the reagent vial is about 0.25 inches by 0.25 inches by 0.25 inches.

7. The apparatus of claim 6 wherein the sample vial has a capacity of 40 milliliters.

8. The apparatus of claim 1 wherein the reagent vial is light-transmitting such that light passes into and out of the reagent vial when the reagent vial is illuminated.

9. The apparatus of claim 1 wherein vapors emanate from the sample and diffuse into contact with the membrane when the reagent vial is in the second position, the vapors including the chemical to be detected.

10. The apparatus of claim 1 wherein the sample directly contacts the membrane when the reagent vial is in the second position.

11. The apparatus of claim 1 wherein a portion of the cap is slid to move the reagent vial between the first and second positions.

12. The apparatus of claim 1 wherein a portion of the cap is rotated to move the reagent vial between the first and second positions.

13. The apparatus of claim 1 wherein the reagent is reactable with the chemical to be detected to form a reaction product in the reagent vial which has at least one detectable property related to the concentration of the chemical.

14. The apparatus of claim 13 wherein the reagent vial is light-transmitting such that light passes into and out of the reagent vial when the reagent vial is illuminated.

15. The apparatus of claim 14 wherein the cap is receivable into an analyzer which includes:

a light source for generating light which is directed toward the reagent vial to illuminate the reaction product therein, the illumination of the reaction product resulting in the production of an optical signal related to the concentration of the chemical to be detected, at least some of the optical signal exiting the reagent vial.

16. The apparatus of claim 15 wherein the analyzer further includes:

at least one optical detection element for receiving the optical signal that exits the reagent vial and for generating another signal which also is related to the concentration; and processing electronics for processing the signal generated by the optical detection element to determine a numerical value for the concentration.

17. The apparatus of claim 16 wherein the analyzer further includes a motor and wherein the reagent vial further includes a mixing device which is magnetically couplable to the motor for driving the mixing device to stir the contents of the reagent vial.

18. The apparatus of claim 15 wherein the optical signal is representative of the absorbance of the reaction product.

19. The apparatus of claim 18 wherein the reagent comprises a Fujiwara reagent and wherein the reaction product is the result of the Fujiwara reaction.

20. The apparatus of claim 15 wherein the optical signal is representative of the fluorescence of the reaction product.

21. The apparatus of claim 20 wherein the reagent comprises a Fujiwara reagent and wherein the reaction product is the result of the Fujiwara reaction.

22. Apparatus for chemical detection, comprising:

a cap for coupling with a sample vial containing a sample, the cap defining a passage through which pass vapors from the sample, the vapors including at least one chemical to be detected;

a reagent vial included in the cap, the reagent vial containing a liquid reagent which is reactable with the chemical to form a reaction product having at least one detectable property related to the concentration of the chemical, and the reagent vial including a membrane which retains the liquid reagent and the reaction product above the membrane and within the reagent vial, wherein said membrane is permeable to the chemical to be detected; and means, coupled to the cap, for moving the reagent vial between a first position and a second position, the reagent vial being disposed from the passage when in the first position such that the vapors are prevented from impinging upon the membrane, the reagent vial being aligned with the passage when in the second position such that the vapors are allowed to diffuse into contact with the membrane.

23. The apparatus of claim 22 wherein the cap is expendable.

24. The apparatus of claim 22 wherein the reagent vial is removable from the cap, and the reagent vial is expendable.

25. The apparatus of claim 22 wherein the apparatus is transportable to allow coupling with the sample vial in the field.

26. The apparatus of claim 25 wherein the size of the cap is about one inch by one inch by one inch.

27. The apparatus of claim 26 wherein the size of the reagent vial is about 0.25 inches by 0.25 inches by 0.25 inches.

28. The apparatus of claim 27 wherein the sample vial has a capacity of 40 milliliters.

29. The apparatus of claim 22 wherein the reagent vial is light-transmitting such that light passes into and out of the reagent vial when the reagent vial is illuminated.

30. The apparatus of claim 22 wherein a portion of the cap is slid to move the reagent vial between the first and second positions.

31. The apparatus of claim 22 wherein a portion of the cap is rotated to move the reagent vial between the first and second positions.

32. The apparatus of claim 29 wherein the cap is receivable into an analyzer which includes:

a light source for generating light which is directed toward the reagent vial to illuminate the reaction product therein, the illumination of the reaction product resulting in the production of an optical signal related to the concentration of the chemical to be detected, at least some of the optical signal exiting the reagent vial.

33. The apparatus of claim 32 wherein the analyzer further includes:

at least one optical detection element for receiving the optical signal that exits the reagent vial and for generating another signal which also is related to the concentration; and processing electronics for processing the signal generated by the optical detection element to determine a numerical value for the concentration.

34. The apparatus of claim 33 wherein the analyzer further includes a motor and wherein the reagent vial further includes a mixing device which is magnetically couplable to the motor for driving the mixing device to stir the contents of the reagent vial.

35. The apparatus of claim 32 wherein the optical signal is representative of the absorbance of the reaction product.

36. The apparatus of claim 35 Wherein the reagent comprises a Fujiwara reagent and wherein the reaction product is the result of the Fujiwara reaction.

37. The apparatus of claim 32 wherein the optical signal is representative of the fluorescence of the reaction product.

38. The apparatus of claim 37 wherein the reagent comprises a Fujiwara reagent and wherein the reaction product is the result of the Fujiwara reaction.

39. Apparatus for chemical detection, comprising:

a cap for coupling with a sample vial containing a sample which includes at least one chemical to be detected;

a reagent vial includes in the cap, the reagent vial containing a liquid reagent and including a membrane which retains the liquid reagent above the membrane, wherein said membrane is permeable to the chemical to be detected; and movable means coupled to the cap and being movable between a first position and a second position, the chemical being allowed to permeate the membrane and enter the reagent vial when the movable means is in the second position, the chemical being prevented from permeating the membrane and entering the reagent vial when the movable means is in the first position.

40. The apparatus of claim 39 wherein the movable means comprises a plug.

41. The apparatus of claim 40 wherein the movable means further comprises a cam assembly coupled to the plug wherein turning of the cam assembly causes movement of the plug.

42. The apparatus of claim 39 wherein the movable means comprises a portion of the cap which slides and thereby causes the reagent vial to move between the first and second positions.

43. The apparatus of claim 39 wherein the movable means comprises a portion of the cap which rotates and thereby causes the reagent vial to move between the first and second positions.

44. The apparatus of claim 39 wherein the cap is expendable.

45. The apparatus of claim 39 wherein the reagent vial is removable from the cap, and the reagent vial is expendable.

46. The apparatus of claim 39 wherein the apparatus is transportable to allow coupling with the sample vial in the field.

47. The apparatus of claim 46 wherein the size of the cap is about one inch by one inch by one inch.

48. The apparatus of claim 47 wherein the size of the reagent vial is about 0.25 inches by 0.25 inches by 0.25 inches.

49. The apparatus of claim 48 wherein the sample vial has a capacity of 40 milliliters.

50. The apparatus of claim 39 wherein the reagent vial is light-transmitting such that light passes into and out of the reagent vial when the reagent vial is illuminated.

51. The apparatus of claim 39 wherein the reagent is reactable with the chemical to be detected to form a reaction product in the reagent vial which has at least one detectable property related to the concentration of the chemical.

52. The apparatus of claim 51 wherein the reagent vial is light-transmitting such that light passes into and out of the reagent vial when the reagent vial is illuminated.

53. The apparatus of claim 52 wherein the apparatus is receivable into an analyzer which includes:

a light source for generating light which is directed toward the reagent vial to illuminate the reaction product therein, the illumination of the reaction product resulting in the production of an optical signal related to the concentration of the chemical to be detected, at least some of the optical signal exiting the reagent vial.

54. The apparatus of claim 53 wherein the analyzer further includes:

at least one optical detection element for receiving the optical signal that exits the reagent vial and for generating another signal which also is related to the concentration; and processing electronics for processing the signal generated by the optical detection element to determine a numerical value for the concentration.

55. The apparatus of claim 54 wherein the analyzer further includes a motor and wherein the reagent vial further includes a mixing device which is magnetically couplable to the motor for driving the mixing device to stir the contents of the reagent vial.

56. The apparatus of claim 53 wherein the optical signal is representative of the absorbance of the reaction product.

57. The apparatus of claim 56 wherein the reagent comprises a Fujiwara reagent and wherein the reaction product is the result of the Fujiwara reaction.

58. The apparatus of claim 53 wherein the optical signal is representative of the fluorescence of the reaction product.

59. The apparatus of claim 58 wherein the reagent comprises a Fujiwara reagent and wherein the reaction product is the result of the Fujiwara reaction.

60. The apparatus of claim 1 wherein the reagent vial further includes a mixing device which is magnetically couplable to a motor for driving a mixing device to stir the contents of the reagent vial.

61. The apparatus of claim 22 wherein the reagent vial further includes a mixing device which is magnetically couplable to a motor for driving the mixing device to stir the contents of the reagent vial.

62. The apparatus of claim 39 wherein the reagent vial further includes a mixing device which is magnetically couplable to a motor for driving the mixing device to stir the contents of the reagent vial.

\* \* \* \* \*